US00PP22068P2

(12) United States Plant Patent
Podaras

(10) Patent No.: US PP22,068 P2
(45) Date of Patent: Aug. 9, 2011

(54) ***BUDDLEJA* PLANT NAMED 'PODARAS #2'**

(50) Latin Name: ***Buddleja crispa*×*Buddleja marubiafolia***
Varietal Denomination: Podaras #2

(75) Inventor: Peter Podaras, Ithaca, NY (US)

(73) Assignee: Cornell University, Ithaca, NY (US)

( * ) Notice: Subject to any disclaimer, the term of this patent is extended or adjusted under 35 U.S.C. 154(b) by 0 days.

(21) Appl. No.: 12/660,643

(22) Filed: Mar. 2, 2010

(51) Int. Cl.
*A01H 5/00* (2006.01)

(52) U.S. Cl. ..... Plt./242

(58) Field of Classification Search ..... Plt./242
See application file for complete search history.

*Primary Examiner* — Susan B McCormick Ewoldt
(74) *Attorney, Agent, or Firm* — C. A. Whealy

(57) ABSTRACT

A new and distinct cultivar of *Buddleja* plant named 'Podaras #2', characterized by its upright plant habit; freely flowering habit; sterile orange-colored flowers; and good garden performance.

1 Drawing Sheet

Botanical designation: *Buddleja crispa*×*Buddleja marubiafolia.*

Cultivar denomination: 'PODARAS #2'.

BACKGROUND OF THE INVENTION

The present invention relates to a new and distinct cultivar of *Buddleja* plant, botanically known as *Buddleja crispa*× *Buddleja marubiafolia* and hereinafter referred to by the name 'Podaras #2'.

The new *Buddleja* plant is a product of a planned breeding program conducted by the Inventor in Ithaca, N.Y. The objective of the breeding program was to create new compact and sterile *Buddleja* plants with unique and attractive flower coloration.

The new *Buddleja* plant originated from a cross-pollination on Mar. 9, 2005 in Ithaca, N.Y., of an unnamed selection of *Buddleja crispa*, not patented, as the female, or seed, parent with an unnamed selection of *Buddleja marubiafolia*, not patented, as the male, or pollen, parent. The new *Buddleja* plant was discovered and selected by the Inventor as a single flowering plant within the progeny of the stated cross-pollination in a controlled environment in Ithaca, N.Y. in August, 2005.

Asexual reproduction of the new *Buddleja* plant by cuttings in a controlled greenhouse environment in West Chicago, Ill. since February, 2008, has shown that the unique features of this new *Buddleja* plant are stable and reproduced true to type in successive generations.

SUMMARY OF THE INVENTION

Plants of the new *Buddleja* have not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Podaras #2'. These characteristics in combination distinguish 'Podaras #2' as a new and distinct *Buddleja* plant:

1. Upright plant habit.
2. Freely flowering habit.

3. Sterile orange-colored flowers.
4. Good garden performance.

Plants of the new *Buddleja* differ from plants of the female parent selection in the following characteristics:

1. Plants of the new *Buddleja* are more vigorous and taller than plants of the female parent selection.
2. Plants of the new *Buddleja* have larger leaves than plants of the female parent selection.
3. Inflorescences of plants of the new *Buddleja* are broader and more branched than inflorescences of plants of the female parent selection.

Plants of the new *Buddleja* differ from plants of the male parent selection in the following characteristics:

1. Plants of the new *Buddleja* are more compact than plants of the male parent selection.
2. Plants of the new *Buddleja* have smaller leaves than plants of the male parent selection.
3. Inflorescences of plants of the new *Buddleja* are denser than inflorescences of plants of the male parent selection.
4. Plants of the new *Buddleja* and the male parent selection differ in flower color as plants of the male parent selection have light pink-colored flowers.

Plants of the new *Buddleja* can be compared to plants of *Buddleja weyeriana* 'Honeycomb', not patented. In side-by-side comparisons, plants of the new *Buddleja* and 'Honeycomb' differed in the following characteristics:

1. Plants of the new *Buddleja* were more compact than plants of 'Honeycomb'.
2. Plants of the new *Buddleja* and 'Honeycomb' differed in leaf color as plants of 'Honeycomb' had dark green-colored leaves.
3. Inflorescences of plants of the new *Buddleja* were flatter and broader than inflorescences of plants of 'Honeycomb'.
4. Plants of the new *Buddleja* and 'Honeycomb' differed in flower color as plants of 'Honeycomb' had yellow-colored flowers.

BRIEF DESCRIPTION OF THE PHOTOGRAPHS

The accompanying colored photographs illustrate the overall appearance of the new *Buddleja* plant, showing the colors as true as it is reasonably possible to obtain in colored reproductions of this type. Colors in the photographs may differ slightly from the color values cited in the detailed botanical description which accurately describe the colors of the new *Buddleja* plant.

The photograph at the bottom of the sheet comprises a side perspective view of a typical flowering plant of 'Podaras #2' grown in a container.

The photograph at the top of the sheet is a close-up view of a typical inflorescence of 'Podaras #2'.

DETAILED BOTANICAL DESCRIPTION

The aforementioned photographs and following observations, measurements and values describe plants grown in Arroyo Grande, Calif. under commercial practice during the summer in one-gallon containers in a polyethylene-covered greenhouse with day temperatures averaging 21° C. and night temperatures averaging 7° C. Plants were pinched two times and were one year old when the photographs and description were taken. In the following description, color references are made to The Royal Horticultural Society Colour Chart, 2007 Edition, except where general terms of ordinary dictionary significance are used.

Botanical classification: *Buddleja crispa*×*Buddleja marubiafolia* 'Podaras #2'.

Parentage:

*Female, or seed, parent.*—Unnamed selection of *Buddleja crispa*, not patented.

*Male, or pollen, parent.*—Unnamed selection of *Buddleja marubiafolia*, not patented.

Propagation:

*Type.*—By cuttings.

*Time to initiate roots plant, summer.*—About 21 days at temperatures of 18° C. to 24° C.

*Time to initiate roots plant, winter.*—About 25 to 30 days at temperatures of 18° C. to 24° C.

*Time to produce a rooted plant, summer.*—About 40 days at temperatures of 18° C. to 24° C.

*Time to produce a rooted plant, winter.*—About 45 days at temperatures of 18° C. to 24° C.

*Root description.*—Fibrous, fine; white in color.

*Rooting habit.*—Freely branching; moderately dense.

Plant description:

*Plant form/habit.*—Deciduous perennial shrub; upright plant habit; narrow inverted triangle; vigorous growth habit.

*Plant height.*—About 42 cm.

*Plant width (spread).*—About 27 cm by 30 cm.

*Lateral branches.*—Quantity: About eight main branches per plant. Length: About 38 cm. Diameter: About 6 mm. Internode length: About 3.5 cm to 4 cm. Strength: Strong. Texture, developing stems: Lanulose to tomentose. Texture, mature stems: Smooth, glabrous. Color, developing: Close to 199A to 199B. Color, mature: Close to 196D.

Foliage description:

*Arrangement.*—Opposite, simple.

*Length.*—About 5.5 cm.

*Width.*—About 3.1 cm.

*Shape.*—Narrowly ovate.

*Apex.*—Broadly acute.

*Base.*—Attenuate.

*Margin.*—Dentate.

*Texture, upper surface.*—Lanulose.

*Texture, lower surface.*—Tomentose.

*Venation pattern.*—Pinnate, reticulate.

*Color.*—Developing leaves, upper surface: Close to 195B. Developing leaves, lower surface: Close to 195D. Fully expanded leaves, upper surface: Close to 146D and 147D; venation, close to 146D. Fully expanded leaves, lower surface: Close to 194B; venation, close to 194C.

*Petiole.*—Length: About 1 cm. Diameter: About 4 mm. Texture, upper and lower surfaces: Lanulose. Color, upper surface: Close to 146D. Color, lower surface: Close to 196C.

Flower description:

*Flower type/habit.*—Single rotate and salverform flowers arranged in compound terminal and axillary panicles; flowers face upright and outward; flowers sessile; panicles compact and globular in shape; freely flowering habit with about 34 flower buds and flowers developing per inflorescence.

*Fragrance.*—Faint, sweet.

*Natural flowering season.*—Plants begin flowering about three months after planting; flowering continuous from spring until frost in California.

*Postproduction longevity.*—Flowers last about three to four days on the plant; flowers persistent.

*Flower buds.*—Height: About 1.1 cm. Diameter: About 2.5 mm. Shape: Oblong. Color: Close to 19B.

*Inflorescence height.*—About 3 cm.

*Inflorescence diameter.*—About 2.8 cm.

*Flower diameter.*—About 7 mm.

*Flower depth.*—About 1.2 cm.

*Flower throat, diameter.*—About 1 mm.

*Flower tube, length.*—About 8 mm.

*Flower tube, diameter at base.*—About 3 mm.

*Petals.*—Quantity per flower: Typically four in a single whorl; petals fused into a narrow tube. Lobe length: About 3 mm. Lobe width: About 3 mm. Lobe shape: Roughly spatulate. Lobe apex: Rounded. Lobe margin: Entire. Texture, upper and lower lobe surfaces: Smooth, glabrous. Texture, throat: Slightly pubescent. Texture, tube: Pubescent. Color: Developing petals, upper surface: Close to 23B. Developing petals, lower surface: Close to 25D. Fully expanded petals, upper surface: Close to N25C; venation, close to N25C; color becoming closer to 28A with development. Fully expanded petals, lower surface: Close to N25D; venation, close to N25D. Throat: Close to 28B; venation, close to 28B. Tube: Close to 26C; venation, close to 26C.

*Sepals.*—Quantity per flower: Typically four in a single whorl, fused towards the base; campanulate calyx. Length: About 4 mm. Width: Less than 1 mm. Shape: Lanceolate. Apex: Acute. Margin: Entire. Texture, upper surface: Smooth, glabrous. Texture, lower surface: Tomentose. Color, upper surface: Close to 138B. Color, lower surface: Close to 193C.

*Peduncles.*—Length: About 3.5 cm to 4 cm. Diameter: About 2 mm. Angle: Erect to about 45° from vertical. Strength: Strong. Texture: Tomentose. Color: Close to 190D.

*Reproductive organs.*—Stamens: Quantity per flower: Typically four; filaments adnate to the corolla tube. Filament length: About 1.5 mm. Filament color: Close to 28B. Anther shape: Lanceolate. Anther length: About 1 mm. Anther color: Close to 1C. Pollen amount: None. Pistils: Quantity per flower: One. Pistil length: About 5 mm. Stigma shape: Oval. Stigma color: Close to 138A. Style length: About 2 mm. Style color: Close to 145D. Ovary color: Close to 193C.

*Seed/fruit.*—Flowers of plants of the new *Buddleja* are sterile and seed and fruit development have not been observed.

Disease/pest resistance: Plants of the new *Buddleja* have been not been observed to be resistant to pathogens and pests common to *Buddleja.*

Garden performance: Plants of the new *Buddleja have* been observed to have good garden performance and tolerate rain, wind and temperatures ranging from about 0° C. to about 40° C.

It is claimed:

1. A new and distinct *Buddleja* plant named 'Podaras #2' as illustrated and described.

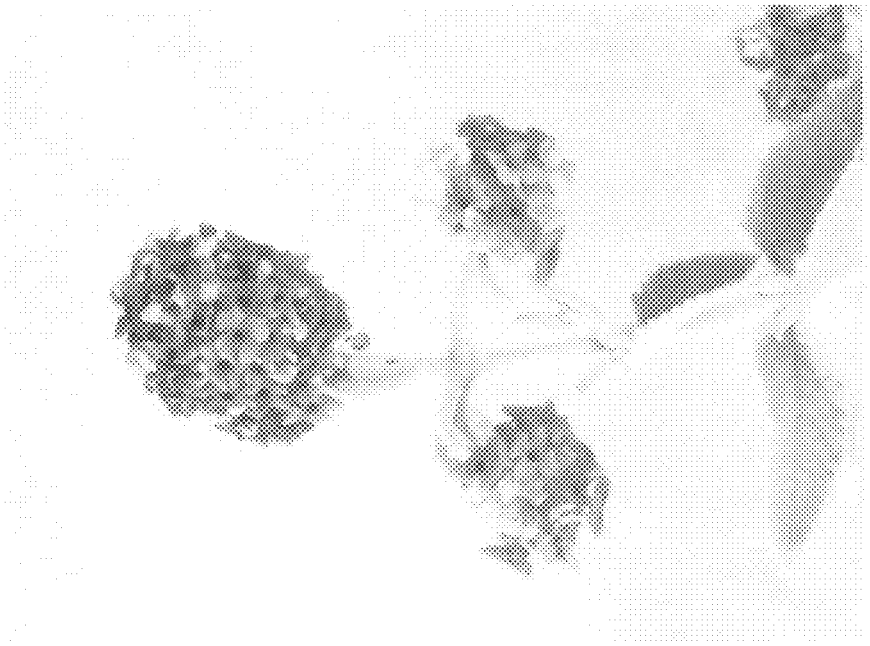
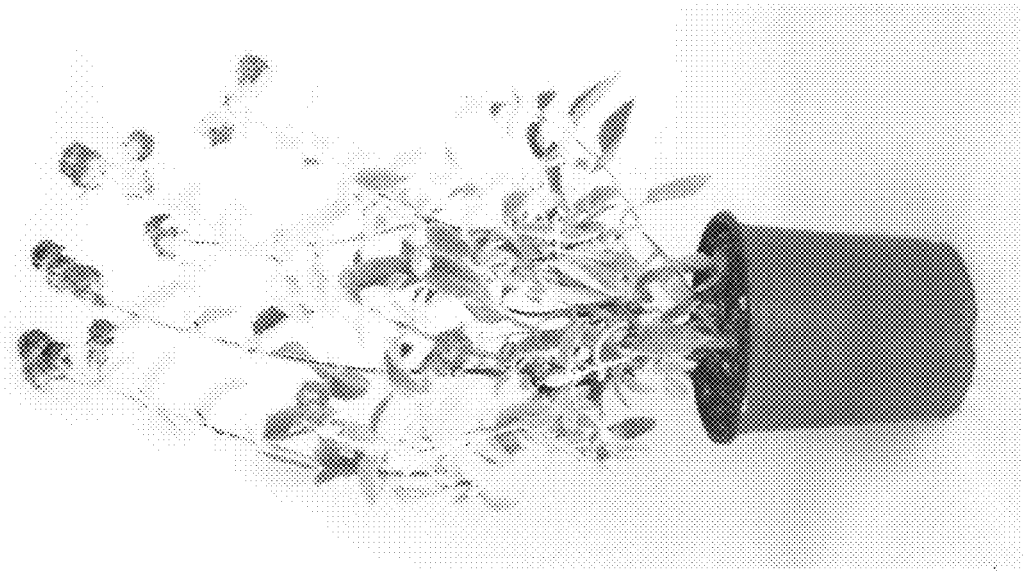

* * * * *